(12) United States Patent
Saxena et al.

(10) Patent No.: US 6,515,001 B2
(45) Date of Patent: Feb. 4, 2003

(54) IL-8 RECEPTOR LIGANDS-DRUGS FOR INFLAMMATORY AND AUTOIMMUNE DISEASES

(75) Inventors: Geeta Saxena, Vancouver (CA); Christopher R. Tudan, Vancouver (CA); Nick Cheng, Coquitlam (CA); Hassan Salari, Delta (CA)

(73) Assignee: Chemokine Therapeutic Corporation, Vancouver (CA)

( * ) Notice: Subject to any disclaimer, the term of this patent is extended or adjusted under 35 U.S.C. 154(b) by 0 days.

(21) Appl. No.: 09/800,422

(22) Filed: Mar. 5, 2001

(65) Prior Publication Data

US 2002/0123483 A1 Sep. 5, 2002

(51) Int. Cl.⁷ .................. C07D 277/30; A61K 31/41
(52) U.S. Cl. .................. 514/365; 548/204; 548/205
(58) Field of Search .................. 548/204, 205; 514/365

(56) References Cited

U.S. PATENT DOCUMENTS

| | | | | |
|---|---|---|---|---|
| 2,530,369 | A | 11/1950 | Simons | 260/621 |
| 2,760,992 | A | 8/1956 | Schoefel et al. | 260/628 |
| 5,807,744 | A | 9/1998 | Berneman et al. | 435/372 |
| 5,856,301 | A | 1/1999 | Craig et al. | 514/12 |
| 5,990,163 | A | 11/1999 | Evans et al. | 514/549 |
| 6,022,848 | A | 2/2000 | Kozlov et al. | 514/6 |
| 6,204,294 | B1 | 3/2001 | Bryan et al. | 514/609 |

OTHER PUBLICATIONS

Hu et al J. Nat. Pro. 1994, 57(1), 42–51 CAS Abstract Only.*
Dunican, A.L. et al., (2000) CXC Chemokine Suppression of Polymorphonuclear Leukocytes Apoptosis and Preservation of Function is Oxidative Stress Independent, *Shock*, vol. 13, pp. 244–250.
Federsppiel, B. et al., (1993) Molecular Cloning of the cDNA and Chromosomal Localization of the Gene for a Putative Seven–Transmembrane segment (7–TMS) Receptor Isolated from Human Spleen, *Genomics*, vol. 16, pp. 707–712.
Furuichi, K. et al., (2000) Distinct Expression of CCR1 and CCR5 in Glomerular and Interstitial Lesions of Human Glomerular Diseases, *Am. J. Nephrol.*, vol. 20, pp. 291–299.
Gimbrone, M.A., Jr. et al., (1989) *Science*, vol. 246, pp. 1601–1603.
Gong, Jiang–Hong et al., (1996) RANTES and MCP–3 Antagonists Bind Multiple Chemokine Receptors, *Journal of Biological Chemistry*, vol. 271 (18), pp. 10521–10527.
Hesselgesser, J. et al., (1998) Identification and Characterization of Small Molecule Functional Antagonists of the CCR1 Chemokine Receptor, *Journal of Biological Chemistry*, vol. 273 (25) pp. 15687–15692.
Holmes, W.E. et al., (1991) *Science*, vol. 253, pp. 1278–1280.
Huber, A.R. et al., (1991) *Science*, vol. 254, pp. 99–102.
Imai, T. et al., (1997) The T Cell–directed CC Chemokine TARC Is a Highly Specific Biological Ligand for CC Chemokine Receptor 4, *Journal of Biological Chemistry*, vol. 272(23), pp. 15036–15042.
Imai, T. et al., (1998) Macrophage–derived Chemokine Is a Functional Ligand for the CC Chemokine Receptor 4, *Journal of Biological Chemistry*, vol. 273(3), pp. 1764–1768.
Jones, S.A. et al. ,(1997) Chemokine Antagonists That Discriminate between Interleukin–8 Receptors, *Journal of Biological Chemistry*, vol. 272(26) pp. 16166–16169.
Kitaura, M. et al., (1996) Molecular Cloning of Human Eotaxin, and Eosinopil–selective CC Chemokine, and Identification of a Specific Eosinopil Eotaxin Receptor, CC Chemokine Receptor 3, *Journal of Biological Chemistry*, vol. 27(13), pp. 7725–7730.
Koch, A.E. et al., (***) *Science*, vol. 258, pp. 1798–1801.
Kurjan, J. et al., (1982) Structure a Yeast Pheromone Gene (MF α): A Putative α–Factor Percursor Contains Four Tandem Copies of Mature α–Factor, *Cell*, vol. 30, pp. 933–943.
Larsen, C.G. et al., (1989) *Science* vol. 243, pp. 1464–1466.
Loetscher, M. et al., (1994) Cloning of a Human Seven–transmembrane Domain Receptor, LESTR, That is Highly Expressed in Leukocytes, *Journal of Biological Chemistry*, vol. 269, pp. 232–237.
Murphy, P.M. & Tiffany, H.L. (1991) *Science*, vol. 253, pp. 1280–1283.
Myers, S.J. et al., (1995) Signal Transduction and Ligand Specificity of the Human Monocyte Chemoattractant Protein–1 Receptor in Transfected Embryonic Kidney Cells, *Journal of Biological Chemistry*, vol. 270(11), pp. 5786–5792.
Neote, K. et al., (1993) Molecular Cloning, Functional Expression, and Signaling Characteristics of a C–C Chemokine Receptor, *Cell*, vol. 72, pp. 415–425.

(List continued on next page.)

Primary Examiner—Joseph K. McKane
Assistant Examiner—Kamal Saeed
(74) Attorney, Agent, or Firm—Bret E. Field; Bozicevic, Field & Francis (57) ABSTRACT

The invention provides therapeutic and biological uses of chemokine-receptor-binding compounds (including chemokine receptor ligands such as chemokine receptor agonists or antagonists), such as benzopyrone derivatives, including uses in the treatment of disease states mediated by chemokines. The relevant chemokine may for example be interleukin-8 (IL-8), and the relevant chemokine receptors may for example be corresponding chemokine receptors (CXCR-1 and/or CXCR-2). In other aspects, the invention provides corresponding pharmaceutical compositions and therapeutic methods. In one aspect, for example, the invention provides for the use of [7-[benzopyrone-5'(3'-amino)-thiazole]-phenylalanine-benyl ester in the treatment of disease.

8 Claims, 2 Drawing Sheets

OTHER PUBLICATIONS

Richmond et al., (1986) *J. Cell Physiology*, vol. 129, p. 375.

Schall, T.J. et al., 1990) Selective attraction of monocytes and T lymphocytes of the memory phenotype by cytokine RANTES, *Nature*, vol. 347, pp. 669–671.

Baggiolini, M., (1998) Chemokines and leukocyte traffic, *Nature* vol. 392, pp. 565–568.

Blease, K. et al., (2000) Airway Remodeling is Absent in CCR1–/– Mice During Chronic Fungal Allergic Airway Disease, *Journal of Immunology*, vol. 165 pp. 1564–1572.

Bleul, C.C. et al., (1996) The lymphocyte chemoattractant SDF–1 is a ligand for LESTR/fusin and blocks HIV–1 entry, *Nature*, vol. 382, pp. 829–833.

Choe, H. et al., (1996) The β–Chemokine Receptors CCR3 and CCR5 Facilitate Infection by Primary HIV–1 Isolates, *Cell*, vol. 85, pp. 1135–1148.

Combadiere, C. et al., (1995) Cloning and Functional Expression of a Human Eosinopil CC Chemokine Receptor, *Journal of Biological Chemistry*, vol. 270(27), pp. 16491–16494.

Deng, H. et al., (1996) Identification of a major co–receptor for primary isolates of HIV–1, *Nature*, vol. 381, pp. 661–666.

Doranz, B.J. et al., (1996) A Dual–Tropic Primary HIV–1 Isolate That Uses Fusin and the β–Chemokine Receptors CKR–5, CKR–3, and CKR–2b as Fusion Cofactors, *Cell*, vol. 85, pp. 1149–1158.

Dragic, T. et al., (1996) HIV–1 entry into CD4+ cells is mediated by the chemokine receptor CC–CKR–5, *Nature*, vol. 381, pp. 667–673.

Streiter et al., (1989) Monokine–induced Neutrophil Chemotactic Factor Gene Expression in Human Fibroblasts, *Journal of Biological Chemistry*, vol. 264(18), p. 10621.

Streiter, et al., (1989) *Science*, vol. 243, p. 1467.

Thelen, M. et al., (1988) Mechanism of neutrophil activation by NAF, a novel monocyte–derived peptide agonist, *FASEB J.*, vol. 2, pp. 2702–2706.

Tokuda, A. et al., (2000) Pivotal Role of CCR1–Positive Leukocytes in Bleomycin–Induced Lung Fibrosis in Mice, *Journal of Immunology*, vol. 164, pp. 2745–2751.

Unemori, E.N. et al., (1993) Melanoma Growth–stimulatory Activity/GRO Decreases Collagen Expression by Human Fibroblasts, *J. Biol. Chem.*, vol. 268(2), pp. 1338–1342.

Von Tscharner, V. et al., (1986) Ion channels in human neutrophils activated by a rise in free cytosolic calcium concentration, *Nature*, vol. 324, pp. 369–372.

Warringa, R.A.J. et al., (1991) *Blood*, vol. 77, pp. 2694–2700.

Hu, Chang–Qi et al., "Anti–AIDS Agents, 10.' Acacetin 7–0–β–D–Galactopyranoside, an Anti–HIV Principle from Chrysanthemum Morifolium and a Structure–Activity Correlation With Some Related Flavonoids", *Journal of Natural Products (LLOYDIA)*, vol. 57, No. 1, 1994, pp. 45–51, XP–001039690 (Abstract).

Zhivolup, A.M. et al., "The high scale screening of isoflavonoids and 4–phenylcoumarins with the use of microorganisms", *Biopolimery I Kletka* (1998), 14(6), pp. 553–558, XP–002203566 (Abstract).

Guo, Anan et al., "Syntheses and antiarrhythmic activity of 4'–methylflavone derivatives", *Zhongguo Yiyao Gongye Zazhi* (1989), 20(8), pp. 349–351, XP002203567 (Abstract).

Li, Bao Qun et al., "The flavonoid baicalin exhibits anti–inflammatory activity by binding to chemokines", *Immunopharmacology*, vol. 49, No. 3, Sep. 2000, pp. 295–306, XP002203565.

Garazd, Ya. L. et al., "Amino acid derivatives of 2–R–7–hydroxy–3', 4'–ethylenedioxyisoflavones", *Chemistry of Natural Compounds (Translation of Khimiya Prirodnykh Soedinenii)* (1999), 35(3), pp. 301–304, XP001079766.

Garazd, M.M. et al., "Amino acid derivatives of 3–phenoxychromones", *Chemistry of Natural Compounds (Translation of Khimiya Prirodnykh Soedinenii)* (2001), 37(1), pp. 32–38, XP001079767.

Ogorodniichuk, A.S. et al., "Synthesis and properties of 3–fluorophenoxy–7–0–aminoacylchromones", *Bioorg. Khim.* (1991), 17(7), pp. 1005–1007, XP002203568.

\* cited by examiner

Figure 1. Inhibition of $^{125}$I-IL-8 Receptor Binding by CTCM192

Figure 2. Inhibition of IL-8-induced Calcium Mobilization by CTCM192

IL-8 RECEPTOR LIGANDS-DRUGS FOR INFLAMMATORY AND AUTOIMMUNE DISEASES

FIELD OF THE INVENTION

This invention relates to therapeutic organic compounds and uses thereof, particularly the treatment of chemokine and chemokine receptor mediated diseases.

BACKGROUND OF THE INVENTION

Inflammatory reactions are generally characterized by dramatic movement of leukocytes and fluids from the bloodstream into the inflamed tissues. Chemotactic factors such as C5a, leukotriene B4 (LTB4), and platelet-activating factor (PAF) are thought to mediate the migration of all types of leukocytes in inflammation. However, pathologically, it has been suggested that the types of infiltrating cell populations will vary depending largely upon the stimuli and the interval from the injury (Chemokines in Disease, *Biology and Clinical Research;* (1999) Edited by Caroline A. Hebèrt; Humana Press, Totowa, N.J.).

Many different names have been applied to Interleukin-eight (IL-8), such as neutrophil attractant/activation protein-one (NAP-1), monocyte derived neutrophil chemotactic factor (MDNCF), neutrophil activating factor (NAF) and T-cell lymphocyte chemotactic factor. IL-8 is understood to be a chemoattractant for neutrophils, basophils and a subset of T-cells. It is thought to be produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP (Baggiolini, M. et. al., (1989) *J. Clin. Invest.* 84, 1045; Schroder, J. et. al., (1987) *J. Immunol.* 139, 3474; ibid, (1990) *J. Immunol.* 144, 2223; Strieter et. al., (1989) *Science* 243: 1467; ibid, (1989) *Journal of Biological Chemistry* 264: 10621; Cassatella et. al., (1992) *Journal of Immunology* 148: 3216).

Chemokines are chemotactic cytokines that belongs to a large family of chemoattractant molecules involved in the directed migration of immune cells (Schall, T. The Chemokines. *In The Chemokine Handbook;* Thompson, A., Ed., Academic Press: San Diego, Calif., 1994; pp419–460). The physiological role generally assigned to chemokines in the immune process is to elicit mobilization of immune cells against pathogenic organisms by direct recruitment and activation. Based on their structural similarity, chemokines may be subdivided into four subfamilies, CXC, CC, C and $CX_3C$, depending on the position of their first two cysteine residues.

In addition to IL-8, GRO-α, GRO-β, GRO-γ and NAP-2 also belongs to the chemokine α-family. Like IL-8, these chemokines have also been referred to by different names. For instance, GRO-α, -β, -γ have been referred to as MGSA-α, -β, and -γ, respectively (Melanoma Growth Stimulating Activity) (Richmond et. al., (1986) *J. Cell Physiology* 129, 375; and Chang et. al., (1992) *J. Immunol.* 148, 451). Current understanding is that all of the chemokines of the α-family which possess the ELR motif directly preceding the CXC motif bind to the IL-8 B receptor.

IL-8, GRO-α, GRO-β, GRO-γ and NAP-2 have been reported to promote the accumulation and activation of neutrophils, and these chemokines have accordingly been implicated in a wide range of acute and chronic inflammatory disorders, including psoriasis and rheumatoid arthritis (Baggiolinni et. al (1992) *FEBS Lett.* 307, 97; Miller et. al., (1992) *Crit. Rev. Immunol.* 12, 17; Oppenheim et. al., (1991) *Annu. Rev. Immunol.* 9, 617; Seitz et. al., (1991) *J. Clin. Invest.* 87, 463; Miller et. al., (1992) *Am. Rev. Respir. Dis.* 146, 427; Donnely et. al., (1993) *Lancet* 341, 6430).

IL-8 has been found to stimulate a number of functions of human neutrophils, including induction of shape change (Thelen, M. et. al., (1988) *FASEB J.* 2, 2702–2706), release of lysosomal enzymes (Peveri, P. et. al., (1988) *J. Exp. Med.* 167, 1547–1559), generation of superoxide (Thelen, M. et. al., (1988) *FASEB J.* 2, 2702–2706), generation of biolipids (Schroder, J. M. (1989) *J. Exp. Med.* 170, 847–863), and increased expression of adhesion molecules on neutrophils (Paccaud, J. P. et. al., (1990) *Biochem. Biophys. Res. Comm.* 166, 187–192). It has chemotactic activity not only for neutrophils but also basophils (White, M. V. et. al. (1989) *Immunol. Lett.* 22, 151–154) and IL-3- or granulocyte-macrophage colony-stimulated factor (GM-CSF)-primed eosinophils (Warringa, R. A. J. et. al., (1991) *Blood* 77, 2694–2700). IL-8 also induces chemotaxis against $CD4^+$ and $CD8^+$ human peripheral blood T lymphocytes (Larsen, C. G. et. al., (1989) *Science* 243, 1464–1466). IL-8 enhances the growth-inhibitory activity of neutrophils to *Candida albicans* (Djeu, J. Y. et. al (1990) *J. Immunol.* 144, 2205–2210).

IL-8 is also thought to act on nonleukocytic cells such as melanoma cells and synovial fibroblasts (Unemori, E. N. et. al., (1993) *J. Biol. Chem.* 268, 1338–1342) in vitro. IL-8 reportedly enhances viral replication, particularly cytomegalovirus, in human fibroblasts in vitro (Murayama, T. et. al., (1994) *J. Virol* 68, 7582–7585). IL-8 may significantly inhibit the antiviral activities of interferon-α (Khabar, A. S. A. et. al., (1996) *Eur. Cytokine Netw.* 7, 554). IL-8 may also increase the adhesion of unstimulated human umbilical cord vein endothelial cells (HUVECs) (Gimbrone, M. A. Jr. et. al., (1989) *Science* 246, 1601–1603), enhance transendothelial migration (Huber, A. R. et. al., (1991) *Science* 254, 99–102) and induce angiogenesis in rat cornea (Koch, A. E. et. al., *Science* 258, 1798–1801).

The production of IL-8 in various human diseases has been extensively studied. Clinically, IL-8 has been identified in skin lesions of psoriasis (Schroder J. M. and Christopher E. (1986) *J. Invest. Dermatol.* 87, 53–58). IL-8 has also been detected in synoval fluids in patients with rheumatoid arthritis (Brennan, F. et. al., (1990) *Eur. J. Immunol.* 20, 2141–2144), osteoarthritis (Symon, J. A. et al., (1992) *Scand. J. Rheumatol.* 21, 92–94; Kaneko, S. et. al., (2000) *Cytokines Cell Mol. Ther.* 6(2) 71–79), and gout (Terkeltaub, R. et. al., (1991) *Arthritis Rheum.* 34, 894–903), suggesting a pathological role for IL-8 in the establishment of arthritis. Increased IL-8 levels have also been detected in other biological fluids such as bronchoalveolar lavage fluids (BALF), pleural fluids (Carrè, P. et. al., (1991) *J. Clin. Invest.* 88, 1802–1810), and urine (Broaddus, V. C. et. al., (1992) *Am. Rev. Repir. Dis.* 146, 825–830). Levels of IL-8 in BALF reportedly increase in patients with adult respiratory distress syndrome (ARDS) (miller, E. J. et. al., (1991) *Am. Rev. Repir. Dis.* 146, 427–432) and idiopathic pulmonary fibrosis (Carrè, P. et. al., (1991) *J. Clin. Invest.* 88, 1802–1810). Elevated serum and bronchoalveolar lavage fluid levels of IL-8 and granulocyte colony-stimulating factor (G-CSF) have been associated with the acute chest syndrome (ACS) in patients with sickle cell disease (Abboud, M. R. et. al., (2000) *Br. J. Haematol.* 111 (2) 482–490). Urinary IL-8 level increase in patients with urosepsis (Olszyna, D. P. et. al., (2000) *J. Infect. Dis.* 182 (6) 1731–1737), urinary tract infection (UTI), and several types of glomerulonephritis such as Ig A nephropathy, acute glomerulonephritis (AGN), purpura nephritis, membranous proliferative glomerulonephritis (MPGN), and lupus nephritis (Wada, T. et. al., (1994) *Kidney Int.* 46, 455–460). These clinical observations have been taken to imply that detection of IL-8 in biofluids from patients may be an important indicator of the acute inflammatory diseases.

Colonization of the gastric mucosa with *Helicobacter pylori* is reportedly associated with a dense infiltration of granulocytes into the lamina propria in the active phase of gastritis. In one study, antral biopsies from 27 patients with *H. pylori*-associated gastritis and 25 from *H. pylori*-negative individuals were analyzed for epithelial cell-derived neutrophil-activating protein 78 (ENA-78) and IL-8 mRNA by semiquantitative reverse transcription (RT)-PCR (Rieder, G. et. al., (2001) *Infect. Immun.* 69(1) 81–88). Only viable *H. pylori* yielded a strong ENA-78 and IL-8 induction, while *H. pylori* outer membrane proteins or water-soluble proteins had no significant effect. These findings may be taken as indicative of the importance of both IL-8 and ENA-78 in the development and perpetuation of *H. pylori* associated gastritis.

Two receptors for IL-8 are expressed on neutrophils: CXCR-1 (IL-8RA/R1) and CXCR-2 (IL-8RB/R2), (Baggiolini, M. et. al., (1997) *Annual Review of Immunology* 15: 675–705). These receptors share 77% amino acid sequence identity, and the respective genes are colocalized on chromosome 2q35 (Holmes, W. E. et. al., (1991) *Science* 253:1278–1280 and Murphy, P. M. and Tiffany, H. L., (1991) *Science* 253: 1280–1283). One receptor, CXCR-2, reportedly has high affinity for IL-8 and all other CXC chemokines that attract neutrophils (e.g. the GRO proteins, NAP-2, etc.), while the other, CXCR-1, reportedly has high affinity for IL-8 only (Baggiolini, M. et. al., (1994) *Adv. Immunol.* 55: 97–179). IL-8 receptors are also found on monocytes, basophils, and eosinophils, but the responses of these cells to IL-8 are much weaker than those of neutrophils (Baggiolini, M. et. al., (1994) *Adv. Immunol.* 55: 97–179).

IL-8 is thought to exert its biological activities by binding to the CXCR-1 and CXCR-2 receptors. Both receptors bind IL-8 with high affinity but have different affinities for MGSA/Groalpha and NAP-2. It has been shown that the expression of epidermal CXCR-2 is increased in psoriasis, suggesting that activation of keratinocytes (KC) mediated by CXCR-2 contributes to the characteristic epidermal changes observed in psoriasis (Kondo, S. et. al., (2000) *J. Cell Physiol.* 183(3): 366–370).

The participation of inflammatory cells in atherosclerosis is a process that is thought to involve chemotactic cytokines, which may play a role in cellularentry into the vessel wall. Consistent with this, IL-8 and its receptor CXCR-2 are expressed on macrophages (Mphi) in atherosclerosis in mice (Boisvert, W. A. et. al., (2000) *Immunol. Res.* 21 (2–3), 129–137).

Xu, L and Fidler, I. J. studied the role of IL-8 in the progressive growth of ovarian cancer cells by isolating high- and low-IL-8-produced from the parental Hey-A8 human ovarian cancer cell lines (Xu, L. and Fidler, I. J. (2000) *Oncol. Res.* 12 (2) 97–106). These studies have been taken to indicate that IL-8 has a direct and indirect growth-potentiating activity in human ovarian cancer cells.

IL-8 (ELR+) was the first CXC chemokine to be found to induce angiogenesis (Keane, M. P. and Strieter, R. M., The Role of CXC Chemokines in the Regulation of Angiogenesis, Mantovani, A. (ed.): (1999) *Chemokines, Chem. Immunol.* Basel, Karger 27: 86–101). IL-8 was shown to mediate both in vitro endothelial cell chemotactic and proliferative activity, as well as in vivo angiogenesis in the absence of preceeding inflammation using bioassays of angiogenesis (Strieter, R. M. et. al., (1992) *American Journal of Pathology* 141: 1279–1284). IL-8 has been found to be significantly elevated in non-small cell lung cancer (NSCLC) (Smith, D. R. et. al., (1994) *Journal of Experimental Medicine* 179: 1409–1415). In Addition, IL-8 was determined to be a major angiogenic factor contributing to overall tumor-derived angiogenic activity in NSCLC (Arenberg, D. A. et. al., (1995) *Journal of Investigation Medicine* 43: (suppl 3) 479A) and in human pancreatic adenocarcinoma (Le, X. et. al., (2000) *J. Interferon Cytokine Res.* 20 (11), 935–946).

SUMMARY OF THE INVENTION

In various aspects, the invention provides methods for the use of chemokine-receptor-binding compounds (which may be chemokine receptor ligands such as chemokine receptor agonists or antagonist), and/or salts thereof, in treating chemokine mediated diseases or chemokine receptor mediated diseases, such as IL-8 mediated diseases, or diseases mediated by chemokine receptors CXCR-1, and CXCR-2.

In some embodiments, the invention relates to methods of using a compound of formula (I), or a pharmaceutically acceptable salt thereof, to formulate a medicament for the treatment of a chemokine mediated disease state, or to treat such a disease:

(Formula I)

(Formula II)

(Formula III)

(Formula IV)

(Formula V)

In the foregoing formulae: "a" may be 0 or an integer from 1 to 4; "b" may be 0 an integer from 1 to 4; "c" at each occurance may independently be 0 or an interger from 1 to 3.

In some embodiments, ring A may be aromatic and may be heterocyclic with one or more heteroatoms selected from the group consisting of oxygen and nitrogen. In Formula I "X" may for example be a hetroatom selected from the group consisting of oxygen and nitrogen. Ring B may be aromatic or non-aromatic and may be substituted at different positions by the groups consisting of alkyl, alkenyls, alkynyls, amino, amido, thio, thiazolo, imidazolo, or aromatic hydrocarbons.

In alternative embodiments, $R_1$ and $R_2$ at each occurance may independently be selected from substituents having 50 or fewer atoms, wherein the substituent may be selected from the group consisting of: H; substituted or unsubstituted alkyls, such as: $C_{1-10}$ alkyls, $C_{1-6}$ alkyls; substituted or unsubstituted cycloalkyls, such as $C_{3-6}$ cycloalkyls; substituted or unsubstituted alkenyls, such as $C_{2-6}$ alkenyls; substituted or unsubstituted alkynyls, such as $C_{2-6}$ alkynyls; substituted or unsubstituted aryls; substituted or unsubstituted heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof.

In alternative embodiments, $R_3$, and $R_4$ at each occurance may independently e selected from substituents having 18 or fewer atoms, wherein the substituent may be selected from the group consisting of: H; substituted or unsubstituted alkyls, such as $C_{1-5}$ alkyls; substituted or unsubstitued cycloalkyls, such as $C_{3-5}$ cycloalkyls; substituted or unsubstitued alkenyls, such as $C_{2-5}$ alkenyls; substituted or unsubstitued alkynyls, such as $C_{2-6}$ alkynyls; substituted or unsubstitued aryls; such as benzyl and benzyl esters; substituted or unsubstitued heterocycles; hydroxyls; aminos; nitros; thiols; primary, secondary or tertiary amines; imines; amides; imidazoles; thiazoles; phosphonates; phosphines; carbonyls; carboxyls; silyls; ethers; thioethers; sulfonyls; sulfonates; selenoethers; ketones; aldehydes; esters; —$CF_3$; —CN; and combinations thereof.

In some embodiments, the chemokine may be selected from the group consisting of: IL-8, and chemokines that bind to a chemokine receptor in a mammal selected from the group consisting of CXCR-1, and CXCR-2.

In various embodiments, the invention provides for the use of compounds of the invention in the treatment of diseases selected from the group consisting of inflammation, chronic and acute:inflammation, psoriasis, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, septic shock, endotoxic shock, urosepsis, glomerulonephritis, lupus nephritis, thrombosis, graft vs. host reaction, angiogenesis, NSCLC, ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of thenerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas and the plaques and tumors of mycosis fungoides and cutaneous T-cell lymphoma/leukemia), and solid tumors arising from lymphomas.

DETAILED DESCRIPTION OF THE INVENTION

In some embodiments, the compounds of the invention may have a chemokine receptor binding affinity $IC_{50}$) below 100 µM, below 50 µM, below 5 µM, below 1 µM, below 100 nM, below 50 nM, below 10 nM or below 1 nM; and may have a selective affinity for a selected chemokine receptor, such as a 10-fold selective affinity, a 50-fold selective affinity or a 100-fold selective affinity, for a selected chemokine receptor relative to an alternative chemokine receptor. For example, in some embodiments, the compounds may have a binding affinity for CXCR-1 and CXCR-2 of below below 50 µM, below 10 µM, below 1000 nM, below 100 nM, below 50 nM, below 10 nM or below 1 nM. Receptor binding affinities may by assayed by any of a number of standard methods, such as competitive displacement of radioactively labeled ligands.

In various aspects, the invention relates to compounds having alternative substitutions and substituent groups, designated in formulae herein as "R", typically with a numeric subscript to identify the substituent group. A substituent group is generally a group that replaces one or more hydrogen atoms attached to a parent structure. The organic substituent groups are for example identified in the Handbook of Chemistry and Physics, 79th Edition, CRC Press (all of which are hereby incorporated by reference). Substituent groups of the invention may for example be selected from groups having from 1 to 100 atoms, such as groups having 100 or fewer, 50 or fewer, 25 or fewer, 20 or fewer, 15 or fewer, 10 or fewer, 5 or fewer, 4, 3, 2, or 1 atom(s). Atoms in such substituents may for example be selected from the group consisting of carbon, hydrogen, oxygen, nitrogen, halogen, sulfur, silicon, arsenic, boron, selenium and phosphorus.

Substituent groups may for example be substituted or unsubstituted alkyls, such as, $C_{1-10}$ alkyls, $C_{1-6}$ alkyls; substituted or unsubstituted cycloalkyls, such as $C_{1-10}$ cycloalkyls, $C_{3-6}$ cycloalkyls; substituted or unsubstituted alkenyls, such as $C_{1-10}$ alkenyls, $C_{2-6}$ alkenyls; substituted or unsubstituted alkynyls, such as $C_{1-10}$ alkynyls, $C_{2-6}$ alkynyls; substituted or unsubstituted aryls; substituted or unsubstituted heterocycles; hydroxyls; aminos; nitros; thiols; primary, secondary or tertiary amines; imines; amides; amino acids; amino esters; phosphonates; phosphines; carbonyls; carboxyls; silyls; ethers; thioethers; sulfonyls; sulfonates; selenoethers; ketones; aldehydes; esters; —$CF_3$; —CN; thiazoles; pyrazoles; and combinations thereof. Substituent groups which are themselves substituted may be substituted with the similar substituents.

In some embodiments, a substituent group may comprise a cyclic, heterocyclic or polycyclic group. The term "cyclic group", as used herein, includes cyclic saturated or unsaturated (optionally aromatic) group having from 3 to 10, 4 to 8, or 5 to 7 carbon atoms. Exemplary cyclic groups include cyclopropyl, cyclobutyl, cyclopentyl, cyclohexyl, and cyclooctyl. Cyclic groups may be unsubstituted or substituted at one or more ring positions. A cyclic group may for example be substituted with halogens, alkyls, cycloalkyls, alkenyls, alkynyls, aryls, heterocycles, hydroxyls, aminos, nitros, thiols, pyroles; thiazoles, pyrazoles; amines, imines, amides, amino acids, amino esters; phosphonates, phosphines, carbonyls, carboxyls, silyls, ethers, thioethers, sulfonyls, sulfonates, selenoethers, ketones, aldehydes, esters, —$CF_3$, —CN.

The term "heterocyclic group" includes cyclic saturated, unsaturated and aromatic groups having from 3 to 10, 4 to 8, or 5 to 7 carbon atoms, wherein the ring structure includes about one or more heteroatoms. Heterocyclic groups may include pyrane, pyrone, pyrrolidine, oxolane, thiolane, imidazole, oxazole, pyrazole, thiazole, piperidine, piperazine, morpholine. The heterocyclic ring may be substituted at one or more positions with such substituents as, for example, halogens, alkyls, cycloalkyls, alkenyls, alkynyls, aryls, other heterocycles, hydroxyl, amino, nitro, thiol, amines, imines, amides, amino acids, amino esters, phosphonates, phosphines, carbonyls, carboxyls, silyls, ethers, thioethers, sulfonyls, selenoethers, ketones, aldehydes, esters, —$CF_3$, —CN. Heterocycles may also be bridged or fused to other cyclic groups as described below.

The term "polycyclic group" as used herein is intended to refer to two or more saturated, unsaturated or aromatic cyclic rings in which two or more carbons are common to two adjoining rings, so that the rings are "fused rings". Rings that are joined through non-adjacent atoms may be termed "bridged" rings. Each of the rings of the polycyclic group may be substituted with such substituents as described above, as for example, halogens, alkyls, cycloalkyls, alkenyls, alkynyls, hydroxyl, amino, nitro, thiol, amines, imines, amides, esters, phosphonates, phosphines, carbonyls, carboxyls, silyls, ethers, thioethers, sulfonyls, selenoethers, ketones, aldehydes, esters, —$CF_3$, or —CN.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl has 20 or fewer carbon atoms in its backbone ($C_1$–$C_{20}$ for straight chain, $C_3$–$C_{20}$ for branched chain), or 10 or fewer carbon atoms. In some embodiments, cycloalkyls may have from 4–10 carbon atoms in their ring structure, such as 5, 6 or 7 carbon rings. Unless the number of carbons is otherwise specified, "lower alkyl" as used herein means an alkyl group, as defined above, having from one to ten carbon atoms in its backbone structure. Likewise, "lower alkenyl" and "lower alkynyl" have chain lengths of ten or less carbons.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group. Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O-aryl. The term "acyloxy" refers to —O—C(O)—$R_7$, in which $R_7$ is alkyl, alkenyl, alkynyl, aryl, aralkyl or heterocyclyl.

The term "amino", as used herein, refers to —N($R_\alpha$)($R_\beta$), in which $R_\alpha$ and $R_\beta$ are each independently hydrogen, alkyl, alkyenyl, alkynyl, aralkyl, aryl, or in which $R_\alpha$ and $R_\beta$ together with the nitrogen atom to which they are attached form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N($R_8$)($R_9$), in which $R_8$ and $R_9$ are as defined above. The term "acylamino"refers to —N($R'_8$)C(O)—$R_7$, in which $R_7$ is as defined above and $R'_8$ is alkyl.

The term "amino acids", as used herein, refers to —CH($N^+H_3$)$COO^-$, in which a substitution could be at either or both 'C' and 'N' positions.

The term 'amino acid esters", as used herein, refers to —CH(NHCOO$R_{10}$)COO—; where $R_{10}$ is defined as above.

As used herein, the term "nitro" means —$NO_2$; the term "halogen" designates —F, —Cl, —Br or —I; the term "sulfhydryl" means —SH; and the term "hydroxyl" means —OH.

The term "aryl" as used herein includes 5-, 6-and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like. Aryl groups can also be part of a polycyclic group. For example, aryl groups include fused aromatic moieties such as naphthyl, anthracenyl, quinolyl, indolyl, and the like.

With reference to Formula I, in one aspect, the compounds of the invention may comprise two hydrophobic aromatic rings, A and B, in which one ring is heterocyclic fused to benzene ring, shown as ring A in Formula I. In some embodiments, substitutions may be made to the hydrophobic aromatic rings that preserve the hydrophobic and aromatic characteristic of the rings, such as the substitution of heteroatoms within the ring or exocyclic substituents. Similarly, substitutions may be made in the bridging moiety such as thiazole substituted in ring A.

In one aspect, the present invention relates to uses of a benzopyrone derivative designated herein as Geetokine:

Geetokine, a benzopyrone derivative (Compound 1)
[7-[5-methylbenzopyrone-5'(3'-methyl)-thiazole]-phenylalanine-benyl ester]
Molecular Formula: $C_{31}H_{26}N_2O_6S$
Molecular Weight: 554.62

EXAMPLES

The following examples are illustrative of various aspects of the invention.

Synthesis of Compound 1

The Geetokine [7-[5-methylbenzopyrone-5'(3'-methyl)-thiazole]-phenylalanine-benyl ester] disclosed herein may be prepared in a variety of ways known to those skilled in the art, including methods adapted from the partial structure disclosed by Biswas, K. M. and Mallik, H (1986, *Phytochemistry* 25(7) 1727–1730).

5-acetonyl-7-hydroxy-2-methylchromone (core structure containing ring 'A' and 'B') is a natural chromone derivative, which may for example be isolated from the flowers of *Cassia siamea* Lam. (Leguminosae). Petroleum extracts and non-basic fractions of the crude extract of *C. siamea* may contain the chromone derivative (also referred to as a benzypyrone derivative).

Compound 1

Allyl chemistry: Benzyl ester of phenylalanine substitution at 7th position of ring 'B' may be accomplished by protecting the hydroxyl group of 7-hydroxy-chromone with an allyl group using an allyl bromide in presence of triethyl amine (TEA) (under basic conditions) and then introducing the benzyl ester of phenylalanine (Z-Phe-OH; CAS# 1161-13-3) in an esterification step.

Thiazole substituion may be introduced by using procedures such as those used in 'still chemistry' of organometallic synthesis. Alternative synthetic methods may be used to synthesize compounds of the invention.

Receptor Binding

Figure 1:
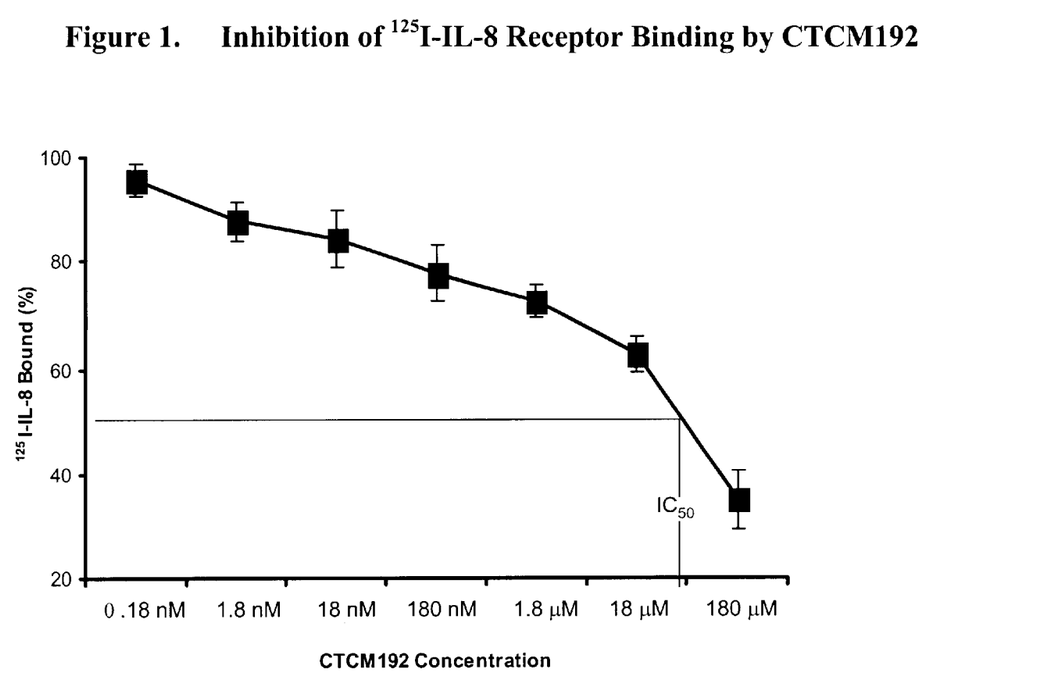
FIG. 1 shows the inhibitory effect of [7-[5-methylbenzopyrone-5'(3'-methyl)-thiazole]-phenylalanine-benyl ester] (designated herein "Geetokine" or CTCM192) on the binding of IL-8 to CXCR-1 and CXCR-2 receptors.

This example discloses the ability of compounds of the invention, such as benzopyrone derivatives, such as CTCM192 (1), to inhibit binding of IL-8 to IL-8 receptors (CXCR-1 and CXCR-2). The binding studies were conducted using $I^{125}$ labeled IL-8 as competitor. FIG. 1 shows the inhibitory effect of compound (1) on the binding of IL-8 to CXCR-1 and/or CXCR-2. The $IC_{50}$ was evaluated at 45 $\mu$M.

Calcium Release

Figure 2:
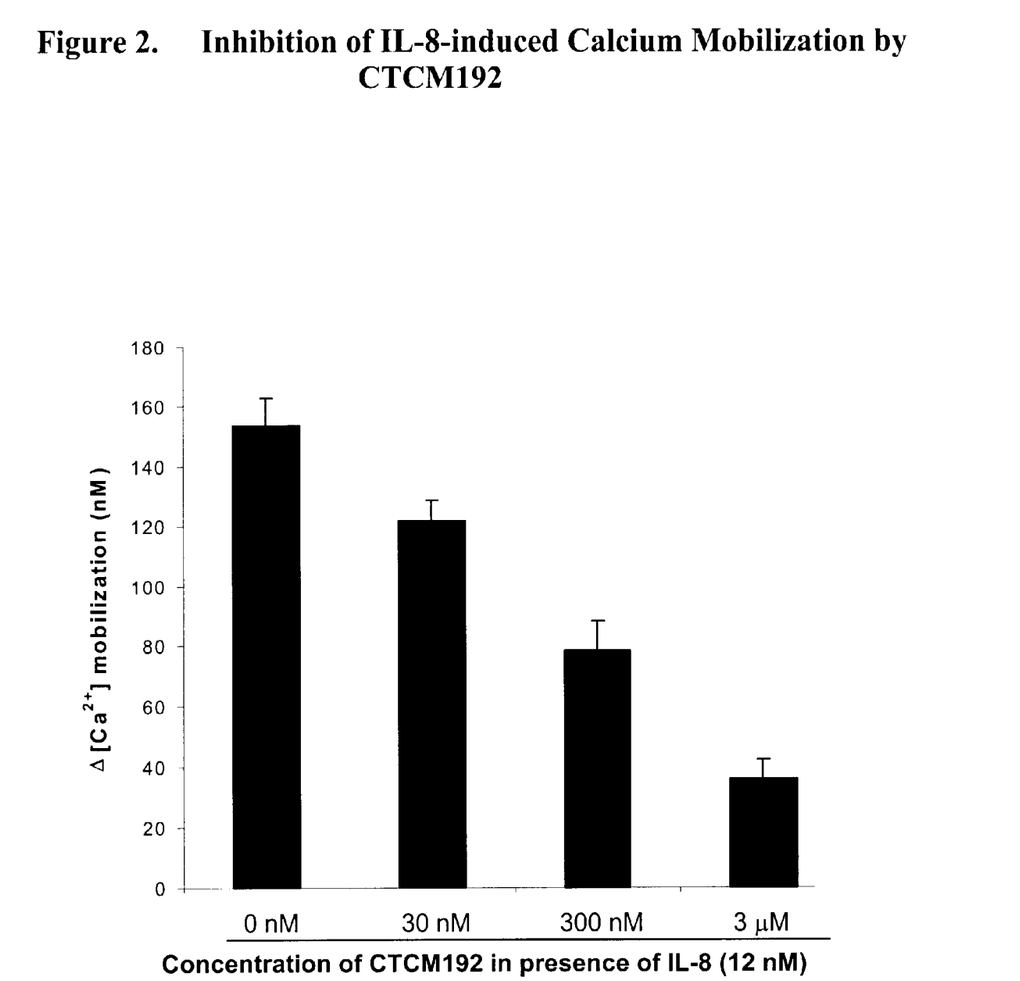
FIG. 2 shows Inhibition effect of CTCM192 on IL-8 induced $[Ca^{+2}]_i$ mobilization.

A rapid, transient rise in the free cytosolic $Ca^{2+}$ concentration ($[Ca^{2+}]_i$) is one of the events associated with the Chemokine mediated induction of the associated receptors and is assumed to be involved in many of the subsequent cellular reactions. Both $Ca^{2+}$ release from intracellular stores and $Ca^{2+}$ influx from the extracellular space contribute to the rise in $[Ca^{2+}]_i$. FIG. 2 shows the inhibition of IL-8-induced intracellular $[Ca^{2+}]_i$ mobilization by CTCM192 in THP1 cells. Fura-2,AM loaded THP1 cells were incubated with CTCM192 for 60 min prior to induction of $[Ca^{2+}]_i$ mobilization by 12 nM IL-8. Results illustrate the effect of CTCM192 (1) on IL-8-induced $Ca^{2+}$ mobilization.

Compound 1 showed an inhibition of IL-8-induced $[Ca^{2-}]_i$ mobilization in THP-1 cells to concentration to 3 $\mu$M where the $IC_{50}$ was evaluated to be 340 nM. In accordance with this aspect of the invention, the benzopyrone derivative, Geetokine, such as compound 1 or corresponding salts may be used for the treatment of a wide range of inflammatory diseases such as gout, arthritis osteoarthritis, rheumatoid arthritis, and ARDS.

Therapeutic Formulations

In one aspect, the invention provides a variety of therapeutic uses for amino-thiazole substituted benzopyrone derivative, such as Geetokine (1). In various embodiments, the compounds of the invention may be used therapeutically in formulations or medicaments for the treatment of CXCR-1 and CXCR-2 mediated diseases. The invention provides corresponding methods of medical treatment, in which a therapeutic dose of a compound of the invention is administered in a pharmacologically acceptable formulation. Accordingly, the invention also provides therapeutic compositions comprising compounds of the invention and a pharmacologically acceptable excipient or carrier. The therapeutic composition may be soluble in an aqueous solution at a physiologically acceptable pH.

The invention provides pharmaceutical compositions (medicaments) containing (comprising) compound of the invention. In one embodiment, such compositions include compound of the invention in an effective amount, meaning a therapeutically or prophylactically effective amount, sufficient to modulate CXCR-1 and CXCR-2 activity, and a pharmaceutically acceptable carrier. In other embodiments, the compositions of the invention may include compound of the invention in a therapeutically or prophylactically effective amount sufficient to modulate the activity of IL-8, and a pharmaceutically acceptable carrier. Compounds of the invention may also be used in combination with other compositions and procedures for the treatment of diseases.

A "therapeutically effective amount" refers to an amount effective, at dosages and for periods of time necessary, to achieve the desired therapeutic result, such as modulation of CXCR-1, CXCR-2 or IL-8 activity. A therapeutically effective amount of a compound of the invention may vary according to factors such as the disease state, age, sex, and weight of the individual, and the ability of compounds of the invention to elicit a desired response in the individual. Dosage regimens may be adjusted to provide the optimum therapeutic response. A therapeutically effective amount is also one in which any toxic or detrimental effects of compounds of the invention are outweighed by the therapeutically beneficial effects.

A "prophylactically effective amount" refers to an amount effective, at dosages and for periods of time necessary, to achieve the desired prophylactic result, such as modulation of CXCR-1, CXCR-2 or IL-8 activity. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In particular embodiments, a preferred range for therapeutically or prophylactically effective amounts of compounds of the invention may be 0.1 nM–0.1 M, 0.1 nM–0.05

M, 0.05 nM–15 µM or 0.01 nM–10 µM. Alternatively, total daily dose may range from about 0.001 to about 100 mg/kg, or up to 10 mg/kg or up to 1 mg/kg of patients body mass. Dosage values may vary with the severity of the condition to be alleviated. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the methods of the invention.

The amount of a compound of the invention in a therapeutic composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylerne glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostear-ate salts and gelatin. Moreover, compounds of the invention can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating compounds of the invention in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, compounds of the invention may be formulated with one or more additional compounds that enhance the solubility of compounds of the invention.

Pharmaceutically acceptable salts include salts that are well known to those skilled in the art such as basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, alicylic acid, phenylacetic acid and mandelic acid. In alternative embodiments, pharmaceutically acceptable cation salts may include alkaline, alkaline earth, ammonium and quaternary ammonium cations.

In accordance with another aspect of the invention, therapeutic compositions of the present invention, comprising a compound of the invention, may be provided in containers having labels that provide instructions for use of compounds of the invention to treat chemokine or chemokine receptor mediated diseases. In some embodiments, such diseases may include inflammation, acute inflammation, chronic inflammation, psoriasis, gout, acute pseudogout, acute gouty arthritis, arthritis, rheumatoid arthritis, osteoarthritis, allograft rejection, chronic transplant rejection, asthma, mononuclear-phagocyte dependent lung injury, idiopathic pulmonary fibrosis, sarcoidosis, focal ischemia, atopic dermatitis, chronic obstructive pulmonary disease, adult respiratory distress syndrome, acute chest syndrome in sickle cell disease, inflammatory bowel disease. Crohn's disease, ulcerative colitis, septic shock, endotoxic shock, urosepsis, glomerulonephritis, thrombosis, graft vs. host reaction, angiogenesis, NSCLC, human ovarian cancer, and human pancreatic adenocarcinoma.

An alternative aspect of the invention, chemokine or chemokine receptor mediated diseases may include cancers susceptible to anti-angiogenic treatment, including both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, blad- der and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects of the invention, compounds of the invention may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, compounds of the invention may be useful in the prevention of metastases from the tumors described above either when used alone or in combination with radiotherapy and/or other chemotherapeutic agents.

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein.

What is claimed is:

1. A method of treating a chemokine mediated disease state, or a disease state mediated by a receptor of the chemokine, in a mammal in need of such treatment, which comprises administering to the mammal an effective amount of a compound of the formula (I), or a pharmaceutically acceptable salt thereof:

(I)

wherein:
"a" is 0 or an integer from 1 to 4;
"b" is 0 or an integer from 1 to 4;
"c" at each occurance is independently 0 or an integer from 1 to 3;
Ring A is aromatic and is heterocyclic, wherein X is one or more heteroatoms selected from the group consisting of oxygen and nitrogen;
Ring B is aromatic or non-aromatic and is substituted at different positions by the groups consisting of alkyl, alkenyl, alkynyl, amino, amido, thio, thiazolo, imidazolo, or aromatic hydrocarbons;
$R_1$ and $R_2$ at each occurance is independently selected from substituents having 50 or fewer atoms, wherein the substituent is selected from the group consisting of: H; substituted or unsubstituted alkyls, $C_{1-10}$ alkyls, $C_{1-6}$ alkyls; substituted or unsubstituted cycloalkyls, $C_{3-6}$ cycloalkyls; substituted or unsubstituted alkenyls, $C_{2-6}$ alkenyls; substituted or unsubstituted alkynyls, $C_{2-6}$ alkynyls; substituted or unsubstituted aryls; substituted or unsubstituted heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof;
$R_3$, at each occurance is independently selected from substituents having 18 or fewer atoms, wherein the substituent is selected from the group consisting of: H; substituted or unsubstituted alkyls, $C_{1-5}$ alkyls; substituted or unsubstituted cycloalkyls, $C_{3-5}$ cycloalkyls; substituted or unsubstituted alkenyls, $C_{2-5}$ alkenyls; substituted or unsubstituted alkynyls, $C_{2-6}$ alkynyls; substituted or unsubstituted aryls; benzyl and benzyl esters; substituted or unsubstituted heterocycles; hydroxyls; aminos; nitros; thiols, primary, secondary or tertiary amines; imines; amides; imidazoles; thiazoles; phosphonates; phosphines; carbonyls; carboxyls; silyls; ethers; thioethers; sulfonyls; sulfonates; selenoethers; ketones; aldehydes; esters; —$CF_3$; —CN; and combinations thereof; $R_4$ is a thiazole; and,
wherein the chemokine is selected from the group consisting of: IL-8, and chemokines that bind to a chemokine receptor in a mammal selected from the group consisting of CXCR-1, and CXCR-2.

2. A method of modulating the activity of a chemokine or a chemokine receptor in host, comprising administering to the host an effective amount of a compound of formula (I), or a pharmaceutically acceptable salt thereof:

(I)

wherein:
"a" is 0 or an integer from 1 to 4;
"b" is 0 or an integer from 1 to 4;
"c" at each occurance is independently 0 or an integer from 1 to 3;
Ring A is aromatic and is heterocyclic, wherein X is one or more heteroatoms selected from the group consisting of oxygen and nitrogen;

Ring B is aromatic or non-aromatic and is substituted at different positions by the groups consisting of alkyl, alkenyl, alkynyl, amino, amido, thio, thiazolo, imidazolo, or aromatic hydrocarbons;

$R_1$ and $R_2$ at each occurance is independently selected from substituents having 50 or fewer atoms, wherein the substituent is selected from the group consisting of: H; substituted or unsubstituted alkyls, $C_{1-10}$ alkyls, $C_{1-6}$ alkyls; substituted or unsubstituted cycloalkyls, $C_{3-6}$ cycloalkyls; substituted or unsubstituted alkenyls, $C_{2-6}$ alkenyls; substituted or unsubstituted alkynyls, $C_{2-6}$ alkynyls; substituted or unsubstituted aryls; substituted or unsubstituted heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof;

$R_3$, is independently selected from substituents having 18 or fewer atoms, wherein the substituent is selected from the group consisting of: H; substituted or unsubstituted alkyls, $C_{1-5}$ alkyls; substituted or unsubstituted cycloalkyls, $C_{3-5}$ cycloalkyls; substituted or unsubstituted alkenyls, $C_{2-5}$ alkenyls; substituted or unsubstituted alkynyls, $C_{2-6}$ alkynyls; substituted or unsubstituted aryls; benzyl and benzyl esters; substituted or unsubstituted heterocycles; hydroxyls; aminos; nitros; thiols; primary, secondary or tertiary amines; imines; amides; imidazoles; thiazoles; phosphonates; phosphines; carbonyls; carboxyls; silyls; ethers; thioethers; sulfonyls; sulfonates; selenoethers; ketones; aldehydes; esters; —$CF_3$; —CN; and combinations thereof; $R_4$ is a thiazole; and, wherein the chemokine is selected from the group consisting of: IL-8, and chemokines that bind to a chemokine receptor in a mammal selected from the group consisting of CXCR-1, and CXCR-2.

3. A method of inhibiting the interaction of a chemokine with a chemokine receptor in a mammal, comprising administering to the mammal an effective amount of a compound of formula (I), or a pharmaceutically acceptable salt thereof:

(I)

wherein:

"a" is 0 or an integer from 1 to 4;

"b" is 0 or an integer from 1 to 4;

"c" at each occurance is independently 0 or an integer from 1 to 3;

Ring A is aromatic and is heterocyclic, wherein X is one or more heteroatoms selected from the group consisting of oxygen and nitrogen;

Ring B is aromatic or non-aromatic and is substituted at different positions by the groups consisting of alkyl, alkenyl, alkynyl, amino, amido, thio, thiazolo, imidazolo, or aromatic hydrocarbons;

$R_1$ and $R_2$ at each occurance is independently selected from substituents having 50 or fewer atoms, wherein the substituent is selected from the group consisting of: H; substituted or unsubstituted alkyls, $C_{1-10}$ alkyls, $C_{1-6}$ alkyls; substituted or unsubstituted cycloalkyls, $C_{3-6}$ cycloalkyls; substituted or unsubstituted alkenyls, $C_{2-6}$ alkenyls; substituted or unsubstituted alkynyls, $C_{2-6}$ alkynyls; substituted or unsubstituted aryls; substituted or unsubstituted heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof;

$R_3$, is independently selected from substituents having 18 or fewer atoms, wherein the substituent is selected from the group consisting of: H; substituted or unsubstituted alkyls, such as $C_{1-5}$ alkyls; substituted or unsubstituted cycloalkyls, $C_{3-5}$ cycloalkyls; substituted or unsubstituted alkenyls, $C_{2-5}$ alkenyls; substituted or unsubstituted alkynyls, $C_{2-6}$ alkynyls; substituted or unsubstituted aryls; benzyl and benzyl esters; substituted or unsubstituted heterocycles; hydroxyls; aminos; nitros; thiols; primary, secondary or tertiary amines; imines; amides; imidazoles; thiazoles; phosphonates; phosphines; carbonyls; carboxyls;

silyls; ethers; thioethers; sulfonyls; sulfonates; selenoethers; ketones; aldehydes; esters; —$CF_3$; —CN; and combinations thereof; $R_4$ is a thiazole; and, wherein the chemokine is selected from the group consisting of: IL-8, and chemokines that bind to a chemokine receptor in a mammal selected from the group consisting of CXCR-1, and CXCR-2.

4. The method of any one of claims 1 through 3, wherein the compound binds to the chemokine receptor with a binding affinity below 100 nM.

5. The method of any one of claims 1 through 4, wherein the chemokine mediated disease is selected from the group consisting of inflammation, chronic and acute inflammation, psoriasis, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, septic shock, endotoxic shock, urosepsis, glomerulonephritis, lupus nephritis, thrombosis, graft vs. host reaction, angiogenesis, NSCLC, ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of the nerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas and the plaques and tumors of mycosis fungoides and cutaneous T-cell lymphoma/leukemia), and solid tumors arising from lymphomas.

6. The method of any one of claims 1 through 5, wherein the compound has the following formula:

7. A pharmaceutical composition comprising a compound of formula (I), or a pharmaceutically acceptable salt thereof, and a pharmaceutically acceptable carrier, excipient or diluent:

(I)

wherein:
"a" is 0 or an integer from 1 to 4;
"b" is 0 or an integer from 1 to 4;
"c" at each occurance is independently 0 or an integer from 1 to 3;
Ring A is aromatic and is heterocyclic, wherein X is one or more heteroatoms selected from the group consisting of oxygen and nitrogen;
Ring B is aromatic or non-aromatic and is substituted at different positions by the groups consisting of alkyl, alkenyl, alkynyl, amino, amido, thio, thiazolo, imidazolo, or aromatic hydrocarbons;

$R_1$ and $R_2$ at each occurance is independently selected from substituents having 50 or fewer atoms, wherein the substituent is selected from the group consisting of: H; substituted or unsubstituted alkyls, $C_{1-10}$ alkyls, $C_{1-6}$ alkyls; substituted or unsubstituted cycloalkyls, $C_{3-6}$ cycloalkyls; substituted or unsubstituted alkenyls, $C_{2-6}$ alkenyls; substituted or unsubstituted alkynyls, $C_{2-6}$ alkynyls; substituted or unsubstituted aryls; substituted or unsubstituted heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof;

$R_3$, is independently selected from substituents having 18 or fewer atoms, wherein the substituent is selected from the group consisting of: H; substituted or unsubstituted alkyls, $C_{1-5}$ alkyls; substituted or unsubstituted cycloalkyls, $C_{3-5}$ cycloalkyls; substituted or unsubstituted alkenyls, $C_{2-5}$ alkenyls; substituted or unsubstituted alkynyls, $C_{2-6}$ alkynyls; substituted or unsubstituted aryls; benzyl and benzyl esters; substituted or unsubstituted heterocycles; hydroxyls; aminos; nitros; thiols; primary, secondary or tertiary amines; imines; amides; imidazoles; thiazoles; phosphonates; phosphines; carbonyls; carboxyls; silyls; ethers; thioethers; sulfonyls; sulfonates; selenoethers; ketones; aldehydes; esters; —$CF_3$; —CN; and combinations thereof; $R_4$ is a thiazole; and, wherein the chemokine is selected from the group consisting of: IL-8, and chemokines that bind to a chemokine receptor in a mammal selected from the group consisting of CXCR-1, and CXCR-2.

8. The pharmaceutical composition of claim 7, wherein the compound has the following formula:

* * * * *

UNITED STATES PATENT AND TRADEMARK OFFICE
CERTIFICATE OF CORRECTION

PATENT NO.    : 6,515,001 B2                                        Page 1 of 1
DATED         : February 4, 2003
INVENTOR(S)   : Saxena, Geeta et al.

It is certified that error appears in the above-identified patent and that said Letters Patent is hereby corrected as shown below:

Column 3,
Line 50, change "cellularentry" with -- cellular entry --.

Column 6,
Line 21, change "e" with -- be --.

Column 7,
Line 1, change "thenerves" with -- the nerves --.
Line 31, delete the word "below".

Column 8,
Line 35, change 'atorns" with -- atoms --.

Column 9,
Line 37, change "$_{R\beta}$" with -- $R_\beta$ --.

Column 16,
Lines 3 and 65, delete "aromatic and is".

Column 17,
Line 61, delete "aromatic and is".

Column 20,
Line 49, delete "aromatic and is".

Signed and Sealed this

Twenty-ninth Day of July, 2003

JAMES E. ROGAN
*Director of the United States Patent and Trademark Office*